United States Patent [19]

Seguin et al.

[11] Patent Number: 4,549,990

[45] Date of Patent: Oct. 29, 1985

[54] MANUFACTURE OF NON-SAPONIFIABLE COMPOUNDS FROM NATURAL SUBSTANCES AND THE RESULTING PRODUCTS

[75] Inventors: Marie-Christine Seguin, Monte Carlo, Monaco; Jean Gueyne, Paris, France

[73] Assignee: Societe dite: Exsymol S.A.M.,

[21] Appl. No.: 488,277

[22] Filed: Apr. 25, 1983

[30] Foreign Application Priority Data

May 14, 1982 [FR] France ................................ 82 08437

[51] Int. Cl.[4] ............................................... C07J 9/00
[52] U.S. Cl. ................................................. 260/397.25
[58] Field of Search .................................... 260/397.25

[56] References Cited

U.S. PATENT DOCUMENTS

| | | | |
|---|---|---|---|
| 2,610,195 | 9/1952 | Gebhart | 260/397.25 |
| 2,897,192 | 7/1959 | Nord | 260/397.25 |
| 2,905,677 | 9/1959 | Fevig et al. | 260/397.25 |
| 2,963,494 | 12/1960 | Cunningham et al. | 260/397.25 |

*Primary Examiner*—Elbert L. Roberts
*Attorney, Agent, or Firm*—Ostrolenk, Faber, Gerb & Soffen

[57] ABSTRACT

Production of non-saponifiable compounds from natural substances such as plants, mushroom mycelium or bacteria, by extraction by means of an organic solvent. The solvent is an aliphatic or aryl ester, the molecule of which comprises at least 10 carbon atoms and preferably more than 12 carbon atoms.

20 Claims, No Drawings

MANUFACTURE OF NON-SAPONIFIABLE COMPOUNDS FROM NATURAL SUBSTANCES AND THE RESULTING PRODUCTS

The present invention relates to an improvement in the production of non-saponifiable compounds from natural substances. It relates particularly to a process of extraction of liposoluble non-saponifiable materials from plants, mushrooms, bacterial mycelia and other natural tissues. More particularly, the invention relates to the manufacture in a sufficiently pure state of products useful in therapeutics, in cosmetics, in foodstuffs or in agriculture, particularly of the sterol, terpene and natural hydrocarbon types. The specific compounds or solutions which this new process allows production of also form part of the invention.

Various non-saponifiable compounds which are found in plants have long formed the subject of industrial extractions for various uses. For example, squalene, carotenoids, various sterols, such as alpha, beta and gamma sito-sterols, stigmasterol, campesterol, ergosterol etc., terpenes, diterpenes, flavone and isoflavone etc. are so produced. These products have found numerous applications in the most varied of fields, ranging for example, from the lubrication of watches and clocks by squalane, made by the hydrogenation of squalene obtained from shark oil, to the treatment of prostate disorders by means of a lipidosterol complex extracted from the African plum, and including numerous cosmetic uses for the non-saponifiable compounds from various oils, such as that of horse-hair, avocado, carob seeds, almonds, etc.

The standard method for obtaining non-saponifiable compounds consists in solubilizing the fatty materials of the natural product by means of an alkaline solution, separating the insoluble materials then subjecting them to extraction with a lipophilic solvent, which generally is an ether or a hydrocarbon and particularly a chlorinated hydrocarbon. When combined with the manufacture of a soap or the corresponding fatty acids, this method is economically viable; in other cases, it becomes costly and laborious because of the many operative stages which it comprises. Also, the usual solvents generally do not yield a sufficient purity of the products desired.

Another method is based on the direct treatment of the natural product by means of a solvent for the liposoluble non-saponifiable substances; it is carried out for products other than greases or oils, particularly on leaves, stalks or plant roots. However, the standard solvents also retain more or less of the saponifiable materials which are always present in natural products; the non-saponifiable compounds thus cannot be obtained pure. On the other hand, the use of chlorinated hydrocarbons, some of which are excellent solvents for the products in question, gives rise to toxicity risks; in fact, it is difficult to eliminate completely these solvents for non-saponifiable extracts, even though the presence of halogenated compounds is prejudicial to the stability of the products obtained.

The present invention remedies the defects of the prior art; it renders possible the production of non-saponifiable compounds economically in the state of purity desired, by extraction with solvents starting with the natural substance, without preliminary separation of the saponifiable compounds.

The improvement according to the invention consists in utilizing, as a solvent or diluent alone or in conjunction, an aliphatic or aryl ester, the molecule of which comprises at least 10 carbon atoms and preferably more than 12 C; particularly advantageous are those solvents having $C_{14}$ to $C_{38}$.

The solvents according to the invention comprise, among aliphatic esters, those of fatty acids containing $C_6$ to $C_{30}$ and particularly $C_8$ to $C_{20}$, saturated or unsaturated; the alcohol residue of these esters can range from $C_1$ to $C_{18}$, the preferred residues being those where the number of carbon atoms is from 1 to 8.

Esters can particularly advantageously be employed such as the octanoates, decanoates, undecanoates, laurates, myristates, palmitates, oleates, ricinoleates, linoleates, linolenates, stearates, arachidates, lignocerates, cerotates, cetoleates, erucitates, etc., of methyl, ethyl, propyl, iso-propyl, butyl, amyl, hexyl, octyl, isooctyl, nonyl, lauryl, oleyl and other radicals.

Particularly suitable for carrying out the process according to the invention also are esters of acids obtained by the epoxydation of unsaturated acids, for example undecylenic, palmitoleic, oleic, linoleic and erucic acid etc.; thus esters can be used such as epoxy-undecanoates, epoxy-palmitates, epoxy-stearates and the like. Also, each of the two groups which constitute the ester can carry substituents, for example halogens or hydroxyls.

Although esters of fatty acids are particularly suitable and are readily accessible commercially, it is also possible to employ esters or lower aliphatic acids provided their alcohol residue has a sufficiently elevated molecular weight, the total number of carbons in the molecule being at least 12. Esters are thus utilizable for example such as lauryl acetate, stearyl acetate, octyl, lauryl or palmityl butyrate, octyl, decyl, octadecyl or triglycol caproate, diglycol monocaprylate, glycol monolaurate or propylene glycol.

The esters employed according to the invention can also be glycerides, particularly oils such as olive, copra, maize, litmus (turnsole), soya etc., or animal greases or oils, particularly those obtained from fish or whales. Epoxided glycerides are particularly suitable, for example epoxided soya oil.

As regards aryl acid esters, the phthalates are particularly recommendable. By way of non-limitative example, reference can be made to dimethyl, diethyl, dibutyl, diisobutyl, diamyl, diallyl, di(2-ethyl-hexyl), dihexyl, diheptyl, di-n-octyl, diisooctyl, diisodecyl, dinonyl and didecyl ortho-phthalates, etc.; the double phthalates of butyl and ethyl-hexyl, butyl and isodecyl, n-octyl and n-decyl, butyl and n-octyl, butyl and n-decyl, butyl and nonyl, butyl and benzyl etc.; and dicyclohexyl, dimethylcyclohexyl, di(methyl-glycol), di(butyl-glycol), bis(diethylene-glycol mono-ethyl ether) and like phthalates.

The solvents or diluents according to the invention can be utilized for extraction or purification of non-saponifiable compounds in various ways as follows.

In a first method of operation, the natural product, plant, mushroom mycelium or bacteria or the like, preferably ground, is mixed with the selected solvent and thus maintained in contact with agitation, preferably with heating, until dissolution of the desired non-saponifiable compounds in the solvent has occurred. In the case of esters which only slightly dissolve non-saponifiable compounds at moderate temperatures, particularly from 0° to 50° C., it is preferable to operate above 50° C. A variant of the invention resides in strongly heating between 100° and 180° C., preferably at 110° to 150° C., for a short time, less than one hour or preferably for 10 minutes or less. The residues of the natural product are separated by filtration and/or centrifuging and the solvent is allowed to cool, to recover the non-saponifiable compounds which precipitate, possibly in a crystalline form.

An important method of operating consists in adding to the solvent after the extraction a liquid which is a non-solvent for the non-saponifiable compounds, particularly a liquid such as methanol, in order to make the desired products precipitate. This addition can be carried out on all of the solution or possibly only on the solvent remaining after precipitation of the non-saponifiable compounds by cooling.

As most of the solvents or diluents according to the invention are quite viscous, it is possible to add standard light solvents, such as ether, ketones or hydrocarbons, possibly halogenated. Usually the addition of about 5 to 50 percent of a light solvent suffices to reduce suitably the viscosity of the solution, without affecting the advantageous properties of the esters according to the invention.

A second form of operation first comprises extraction of the non-saponifiable compounds from the natural substance with the aid of one or more standard solvents, such as for example ethyl ether, petroleum ether, chloroform, methylene chloride, dichlorethane, trichloroethylene etc. After evaporation of this solvent, the residue obtained, which contains the desired non-saponifiable compounds generally accompanied by impurities, is treated with an ester according to the invention. The mixture thus formed is treated with a non-solvent such as methanol, which causes precipitation of the non-saponifiable substances in a state of considerably improved purity.

Alternatively, this mixture is first heated as indicated above and then allowed to cool with a view to causing precipitation of the insoluble materials. A new fraction of these can be recovered by the addition of methanol to the remaining solvent.

According to a variant, the natural product is treated with a standard solvent to which an ester according to the invention has been added. The latter then remains in the form of a mixture with the non-saponifiable extracts, after evaporation of the solvent. The sequence of operations is that of the two preceding paragraphs.

If it is desired to isolate the non-saponifiable compounds in a pure state, the process according to the invention allows the use of a solution and/or dispersion of these compounds, that is to say sterols, squalene, carotenoids, diterpenes, flavones or others, in the completely innocuous liquid comprising the ester according to the invention. Thus, for example, sterols in solution and/or dispersion in esters, such as hexyl laurate, ethyl oleate, octyl epoxystearate or epoxided soya oil, can be applied directly in cosmetic or pharmaceutical compositions.

As regards the proportions of the esters according to the invention to be employed to carry out a given extraction, this naturally depends on the nature of the substances in use, particularly the solubility of the non-saponifiable compounds to be extracted in the given ester or esters. In practice, usually the weight of the ester utilized is from 0.2 to 5 parts per part of non-saponifiable compound present. As a general rule, when the ester is employed without a standard solvent, it is suitable to carry out the extraction at a temperature which is higher as the proportion of the ester is lower.

Among the various natural substances suitable for the process of the invention, the following are included by way of example: licorice, ginseng, elder and willow catkins, *Lithospermum ruderale L.* (Gremil), the cruciferae, Peruvian bark, green coffee, Jaborandi (*Pilocarpus pinnatifolius*), parsley, anemone, brewers' yeast, the mycelium of a culture of *Echerichia coli*, etc.

The invention is illustrated by the non-limitative examples which follow:

EXAMPLE 1

Extraction and purification of the liposoluble part of hops.

1 kg of the dried plant is ground and then treated with 5 kg of methylene chloride. After filtration, this solvent is evaporated, which leaves 30 g of residue constituted by a light brown "oleoresin" of a strong odour, not utilizable in cosmetics.

The oleoresin is diluted in 10 g of octyl epoxy-stearate, oxirane index 3.5%, at 60° C. The mixture obtained is treated with 800 ml of methyl alcohol; a greenish-white precipitate then forms which after drying weighs 12.3 g and contains the purified hop sterols and is completely suitable for cosmetological use.

EXAMPLE 2

Preparation of a lipidosterol complex.

1 kg of pulverised African plum bark (*Pygeum africanum*) is agitated with 5 kg of methylene chloride for 1 hour. After filtration, the solvent is evaporated, which leaves a residue of 20 g of impure oleoresin. This residue is diluted with 5 g of octyl epoxy-stearate (oxirane index 3.5%) at 70° C., which renders it sufficiently fluid to be subjected to purification; this is effected by introducing the mixture obtained, while hot, into 200 ml of methanol. A precipitate forms, constituted by the substantially pure sterol. An extra-pure product is obtained following a second operation consisting of again diluting the sterol with 5 g of octyl epoxystearate and again precipitating with the addition of 200 ml of methanol. This product has a very good activity in the treatment of prostatic adenoma.

EXAMPLE 3

Liposoluble part of hops.

As in Example 1, 1 kg of the dried plant is treated with 5 kg of methylene chloride, but this has previously been combined with 15 g of n-butyl laurate. The methylene chloride is evaporated, which leaves a fluid residue of 28 g, constituted by a mixture of n-butyl laurate with the oleoresin extracted from the hops. This product is mixed with 800 ml of methyl alcohol and the whitish-green precipitate obtained is separated and dried; 13 g of hop sterols are thus obtained.

EXAMPLE 4

Sterols of African Plum.

As in Example 2, 1 kg of the bark of *Pygeum africanum* is pulverised and treated with 5 kg of methylene chloride, but to the latter is previously added 7 g of octyl epoxy-stearate having an oxirane index of 3.5%. After separation of the bark powder and evaporation of the methylene chloride, 28 g of an oily product is obtained which is then mixed with 200 ml of methanol to precipitate the non-saponifiable products. After separation of the precipitate and drying, 12 g of sterols of good purity remain.

EXAMPLE 5

Extraction of ginseng steroids.

Dried Panax ginseng roots are finely ground. To 1 kg of the powder, 1 kg of ethyl decanoate is added and the pasty mixture is heated at 95° C. for 26 minutes. Vigorous drying is rapidly effected in the hot state in order to separate the liquid to which is added 100 g of fresh ethyl decanoate, hot, which had served for washing the remaining powder. After cooling to ambient temperature and standing for 24 hours, 64 g of a precipitate was separated, utilizable as such as pharmacy, in view of the complete non-toxicity of the ethyl decanoate.

On the other hand, the separated decanoate itself constitutes a new interesting product, because it contains in solution a certain quantity of the active principles of ginseng and can consequently be employed as such.

EXAMPLE 6

Extract of brewers' yeast.

400 g of methyl stearate diluted with 200 g of ethyl glycol acetate ("Cellosolve" acetate) are added to 1 kg of dry brewers' yeast. The mixture is then heated to 60° C. for 3 hours. The liquid is then separated by centrifuging; after cooling to 0° C. and standing for 10 hours, a useful precipitate which formed is separated, while the solvent is re-utilized for a new operation.

EXAMPLE 7

Parsley extract.

1 kg of fine powder obtained by grinding the dry roots of parsley (*Petroselinum sativum Hoffm*) is mixed with 700 g of pre-heated methyl palmitate; the whole was maintained at 115° C. for 8 minutes with stirring. Rapid but intensive drying is then effected. The remainder of the solvent is recovered by centrifuging the solid residue. The palmitate is allowed to cool to the ambient temperature, which is accompanied by precipitation of a parsley extract; the precipitate is separated, washed with alcohol and used in foodstuffs, while the remaining liquid is re-utilized in a new extraction.

EXAMPLE 8

Extraction of anemone sterols.

1 kg of the entire dry plant, *Anemone pulsatilla* (*Pulsatilla vulgaris Mill.*) is agitated with 4 l of dichloroethane for 3 hours at ambient temperature. After separation of the solvent, the latter is evaporated leaving a residue of 26 g of a dark pasty product. To this residue, 10 g of isopropyl myristate is added and the mixture is homogenized at 40° C.; then 500 ml of methanol is added to it and then the precipitate which forms is recovered and dried, containing sterols of anemone in a particularly pure form.

EXAMPLE 9

Anti-rheumatic composition.

1 kg of dried catkins of the white willow (*Salix alba L.*) are mixed with 4 kg of chloroform and 300 g of dimethyl orthophthalate. The mixture is maintained at 40° C. with agitation for 6 hours. The solvents are separated from the catkins by energetic drying, after which the chloroform is eliminated by distillation. The dimethyl phthalate remains which contains the active principles of the willow catkins; this solution is directly utilizable as an anti-rheumatic liniment.

EXAMPLE 10

100 g of the dry mycelium of *Strepotomyces griseus* are mixed with 250 g of glycerol mono-ricinoleate and the mixture is maintained at 60° C. with stirring for 2 hours. The liquid, still hot, is separated by centrifuging; it constitutes a vitamin composition which is rich in cyano-cobalamine ($B_{12}$) and is directly utilizable.

We claim:

1. Improved process for obtaining liposoluble non-saponifiable compounds selected from the group consisting of sterols, terpenes and hydrocarbons from natural substances, by extraction by means of an organic solvent, characterized in that the solvent is an aliphatic or aryl ester, the molecule of which comprises at least 10 carbon atoms.

2. Process according to claim 1, characterized in that the solvent is a $C_{14}$ to $C_{38}$ ester.

3. Process according to claim 1 or 2, characterized in that the solvent is an aliphatic ester of a $C_6$ to $C_{30}$ saturated or unsaturated fatty acid, the alcohol residue of the ester containing $C_1$ to $C_{18}$.

4. Process according to claim 3, characterized in that the alcohol residue of the ester contains $C_1$ to $C_8$.

5. Process according to claim 4, characterized in that the acid residue of the ester carries an epoxy group.

6. Process according to either of claims 1 or 2, characterized in that the ester is a phthalate.

7. Process according to claim 1, in which the natural substance is treated with a standard light solvent in order to extract the non-saponifiable compounds after which the light solvent is separated and evaporated, characterized in that the residue from this evaporation is taken up in an ester containing at least 10 carbon atoms in its molecule and is then separated from this ester.

8. Process according to claim 7, characterized in that separation of the non-saponfiable compound is effected by treatment of the ester containing it with a non-solvent liquid.

9. Process according to claim 8, characterized in that the non-solvent is methanol.

10. Process according to claim 1, characterized in that the natural substance is mixed with the ester at a temperature of 0° to 150° C., after which the ester is separated and cooled to effect precipitation of the non-saponifiable compounds.

11. Process according to claim 8, characterized in that the ester is treated with methanol after its separation from the natural substance and the precipitate formed is recovered.

12. Process according to claim 1, characterized in that the solvent is selected from the group consisting of octyl epoxy-stearate, n-butyl laurate, ethyl deconoate, methyl stearate, methyl palmitate, isopropyl myristate, dimethyl orthophthalate and glycerol mono-ricinoleate.

13. Process according to claim 7 in which the light solvent is selected from the group consisting of ethyl ether, petroleum ether, chloroform, methylene chloride, dichloroethane and trichloroethylene.

14. Process according to claim 1, in which the non-saponifiable compound is separated by treatment of the ester containing it with a nonsolvent liquid.

15. Process according to claim 14 in which the non-solvent is methanol.

16. Process according to claim 1 in which the natural substance is treated with a mixture of a standard light solvent and the ester, and wherein the light solvent is thereafter evaporated.

17. Process according to claim 16 wherein the light solvent is selected from the group consisting of ethyl ether, petroleum ether, chloroform, methylene chloride, dichloroethane, and trichloroethylene.

18. The process according to claim 16 in which the non-saponifiable compound is separated by treatment of the ester containing it with a nonsolvent liquid.

19. Process according to claim 18 wherein the nonsolvent is methanol.

20. Process according to claim 1 in which 0.2–5 parts of ester per part of liposoluble non-saponifiable compound is heated with the natural substance at 50°–180° C. and thereafter the ester containing dissolved non-saponifiable compound is separated from the natural substance.

* * * * *